United States Patent [19]

McDevitt

[11] 4,112,772
[45] Sep. 12, 1978

[54] DEVICE AND METHOD FOR OBTAINING A SAMPLE OF LIQUID

[76] Inventor: Robert F. McDevitt, Box 551, Ogden Dunes, Portage, Ind. 46368

[21] Appl. No.: 720,697

[22] Filed: Sep. 7, 1976

Related U.S. Application Data

[63] Continuation of Ser. No. 565,396, Apr. 7, 1975, abandoned.

[51] Int. Cl.² ............................................. G01N 1/12
[52] U.S. Cl. ........................ 73/425.4 R; 73/DIG. 9; 249/DIG. 4
[58] Field of Search ............... 73/425.4 R, DIG. 9; 264/4; 249/DIG. 4

[56] References Cited

U.S. PATENT DOCUMENTS

2,515,060  7/1950  Smith ............................... 73/DIG. 9
3,646,816  3/1972  Hance .............................. 73/425.4 R Primary Examiner—S. Clement Swisher

[57] ABSTRACT

Molten metal sampling devices and methods in which a pair of mold halves, held together with a spring clip provide a sample having a generally large portion with a stem and a pair of smaller laterally offset smaller portions joined to the larger portion by thin severable connecting elements. Cylindrical and "T" shaped deoxidizing elements are also disclosed.

30 Claims, 47 Drawing Figures

DEVICE AND METHOD FOR OBTAINING A SAMPLE OF LIQUID

This is a continuation of Ser. No. 565,396 filed Apr. 4, 1975, now abandoned.

DESCRIPTION OF THE TESTING PROCEDURE

In the processing of metals in the molten state it is necessary to obtain a sample representative of the parent material, at various stages in the processing, for the evaluation of either its chemical composition or metallographic structure.

The device or sampler embodying the subject invention is preferably designed to obtain a quick chilled sample from the flowing metal as it is transferred by pouring from one type vessel to another. It is primarily designed to be used where molten steel is poured from a teeming ladle into a mold. The molten steel is teemed through a nozzle in the bottom of the ladle, and the resulting stream is controlled through use of a mechanical, electro, or hydraulic valve arrangement. The diameter of the stream can be from $\frac{3}{4}$ to $3\frac{1}{2}$ depending on the rate of flow desired.

The device also has application in the continuous casting process during transfer of molten metal from ladle to tundish to mold under controlled condition. This device has further application in any area or with any molten metal where the molten metal is transferred from one vessel to another under controlled conditions.

For many years the typical method of sampling molten metal in the steel industry was to use what was defined as a spoon. The spoon consisted of a deep bowl type ladle or sampler attached to the end of a long handle and made of either cast or forged steel. The spoon varied in size and had a lip to facilitate pouring. In practice the pouring stream was controlled to a slow or partial stream and the spoon was then dipped into the stream of metal to obtain the sample. The spoon was usually tipped into either the right or left side of the stream, whichever was most convenient, and partially filled with molten metal. The molten metal content of the spoon was then poured into a small test mold positioned on the platform. The casting from this mold provided a sample 4 inches to 8 inches long, tapered, and 1 inches to 2 inches square in cross-section. The sample could be sawed or drilled in the laboratory to provide samples for wet chemistry analysis, spectographic analysis or metallorgraphic evaluations. The samples obtained as described above are used to represent a portion of the metal in the teeming ladle at given intervals in the pouring process.

This conventional method of sampling is not only wasteful from the standpoint of time and material but also exposes the molten metal to atmospheric oxygen which can cause variations in the chemical content of the sample. The degree of the chemical variation is dependent on the grade of steel as well as the techniques of the individual doing the sampling. The effect is most pronounced with the elements of carbon and manganese with varying effects on other elements. Although the steel industry has been aware of the phenomenon and does make corrections; much could be gained by minimizing this condition. Other disadvantages of this conventional method are the need to arrest the stream and the extreme safety hazards involved with taking a sample when the molten metal stream cannot be controlled.

Advantages of the invention or inventions over the spoon technique are:

1. Minimum exposure of the sample to atmospheric oxygen.
2. Simplified sampling technique eliminating the heavy spoon and repouring technique.
3. Elimination of the need to arrest the molten metal stream flow.
4. Precision cast samples with a quick chill and tailored for minimum preparation.
5. Representative and reproducible results at a minimum of expense.
6. Safe procedure in obtaining samples.

In view of the foregoing, one of the important objects of the invention is to provide an elongated device for obtaining a sample of a liquid, such as molten metal, which comprises, among other things, a pair of half sections forming a chamber, tubular means which has an inner extremity communicatively connected to the chamber and an outer extremity provided with an entrance for initially receiving molten metal for flow into the chamber, means at one extremity of the device for holding the sections together, and means at its opposite extremity for holding the sections and tubular means assembled, and wherein one or both of these holding means may serve to facilitate disassembly of the sections. More particularly in this respect, one of the holding means for the sections comprises clip means, and an appendage held in place by this clip means may be utilized for identificating purposes and effect release of the clip means, and the means for holding the sections and tubular means may be operated to facilitate disassembly of these components.

A significant object of the invention is to provide a device of the character described above in which each section includes a relatively large head portion provided with a recess and an extended portion having a center groove therein so that when the sections are correctly assembled the recesses will form a primary chamber and the grooved extensions will form a tubular formation communicating with the chamber, and the extensions are provided with additional grooves forming secondary chambers for receiving samples of molten metal from the primary chamber.

Also, an object of the invention is to provide a device as described in the preceding paragraph in which the head portions of the sections are also provided with recesses which form additional secondary chambers which receive molten metal from the primary chamber.

A specific object is to provide a device in which the head portions in lieu of forming a primary chamber form a plurality of rows of chambers for receiving molten metal.

An important object of the invention is to provide various forms of connectors which are attachable to a lance and serve to detachably support a device in various operative positions.

More particularly, one of the connectors is in the form of an elongated housing having an end wall structure provided with an opening so that a device can be stored in a retracted or inoperative position in the housing or be shifted to an operative position so that at least a portion of the tubular means of the device can be extended through the opening for use and entry into molten metal, while a different form of connector is elongated and tubular, with one extremity being adapted for connection with a lance and an opposite extremity which is provided with a pair of opposed transverse openings for receiving opposite extremities of a device for locating the latter in an operative position substantially transverse to the lance, including means carried by the connector for locking the device in such position.

A specific object is to provide a connector having locking means, as referred to in the preceding paragraph, in which the connector is preferably constructed of a suitable disposable material, such as pasteboard, and the locking means is preferably in the form of integral wing portions of the connector which can be manually flexed or bent to releasably engage the head portion of the device whereby the latter can be locked in either of two positions to locate the entrance of the tubular means in the desired operative position.

Another specific object of the invention is to provide a modified form of connector which is elongated and tubular so that one extremity can be attached to a lance and an opposite extremity which is provided with a side opening and an opposed side slot whereby extremities of a device can be disposed in the opening and slot, with marginal edges of the slot serving the frictionally engage the head of the device for holding the device in an operative position.

Another important object of the invention is to provide a unique setup whereby a connector is so designed and constructed that a lance and/or connector can be manipulated to releasably hold a device in an operative position relative to the connector.

Another specific object of the invention is to provide different forms of means for holding the sections and tubular means assembled.

Also, an object is to provide a device whereby different forms of sample portions may be obtained. More particularly, one sample may include a large head or stem, and longitudinal and offset portions joined to the head, and others in lieu of a large head include a plurality of relatively small joined round portions or joined parallel portions.

A particularly important objective is to provide a setup whereby a portion of a sample may be severed from a head portion by an improved method.

Additional objects and advantages of the invention reside in providing a device which is safe and efficient to use, durable and comprised of components which can be economically maufactured and assembled on a production basis.

Other objects and advantages will become apparent after the description hereinafter set forth is considered in conjunction with the drawings annexed hereto.

Figure 1:
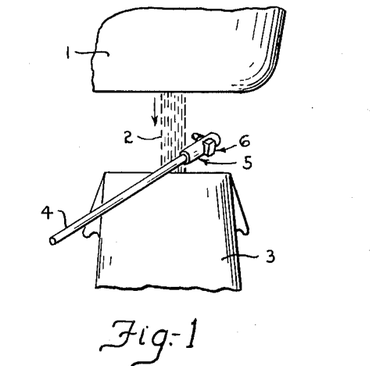
FIG. 1 illustrates a device carried by a lance for use in obtaining a sample of a liquid from a stream thereof.

Referring to FIGS. 1 through 4 and particularly to FIG. 1, there is shown a ladle or vessel 1 containing a hot fluid, such as molten metal, which flows in a stream 2 into a mold 3. A lance 4 is provided with a connector, generally designated 5, and a device generally designated 6, is detachably connected to the connector, and provided with tubular means 7 for disposition in the stream 2 for obtaining a sample therefrom.

The lance 4 is preferably of a length to facilitate manipulation of the device and protect an operator and may be constructed of any material suitably for the purpose but is preferably in the form of an elongated length of pipe 1.

Figure 2:
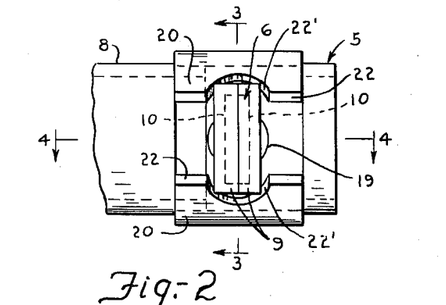
FIG. 2 is a partial side view of a connector on the lance showing one mode of attaching the device to the connector.
Figure 3:
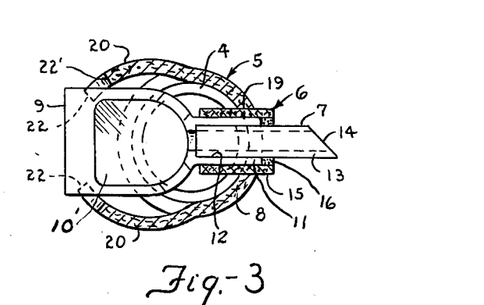
FIG. 3 is a transverse section taken substantially on line 3—3 of FIG. 2.
Figure 4:
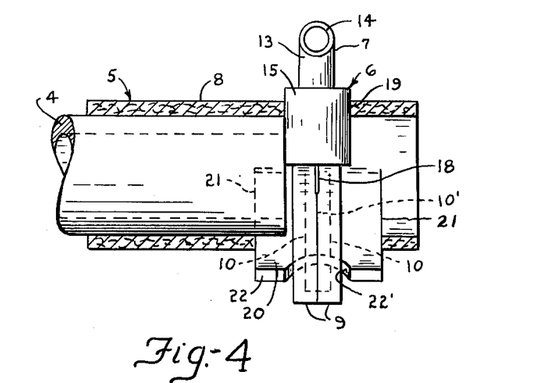
FIG. 4 is a longitudinal section taken substantially on line 4—4 of FIG. 2.

The connector 5, may be designed and constructed in various ways as will appear hereinafter, but as best shown in FIGS. 2, 3 and 4, it is preferably in the form of a tubular cylindrical member 8 of pasteboard or equivalent material. One extremity of the connector is snugly fitted over an end of the lance and its other extremity serves to detachably support the device 6 in a position transverse to the longitudinal axis of the connector and/or lance.

Figure 16:
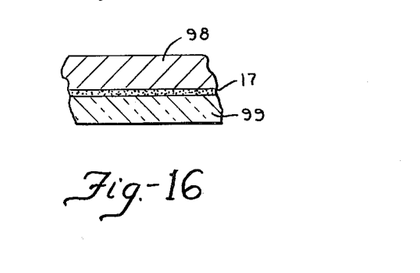
FIG. 16 is an enlarged partial section showing a way of securing components of the device of FIG. 15 together.

The device 6 is elongated and is preferably comprised of a pair of moulded half sections, each having an enlarged or head portion 9 provided with a recess 10, and a reduced extended portion 11 provided with a semi-cylindrical groove 12. When the sections are correctly assembled, the recesses define a chamber 10' and the extended portions 11 and grooves 12 define a tubular formation. The device also preferably includes a tubular means 13, preferably in the form of a cylindrical tube of Pyrex, quartz or equivalent material which has an inner extremity secured in the opening and an outer free extremity provided with a bevelled inlet or entrance 14 for entry into the stream 2. A tubular casing or sleeve 15, preferably of pasteboard, is snugly fitted about the extended portions 11 of the half sections whereby to hold the sections assembled and so that the tubular means 7 is more or less clamped between the extended portions. An apertured member 16 or cement preferably surrounds the tubular means 7 and is snugly fitted or packed into the sleeve and against the portions 11 whereby to prevent entry of molten metal between the sleeve and portions 11 and between the latter and the tubular means. A layer of cement 17, as depicted in FIG. 16, may also be utilized to secure a tubular means in a tubular formation or a casing about the tubular formation. It should be noted that the sections are provided with mating notches whereby to provide vents 18 (one shown) at the sides of the heads 9. It may also be noted that the head portions having planar parallel side surfaces, planar end surfaces and rounded surfaces which merge into the extended portions 11. The extended portions may be referred to as channel portions which form a tubular formation which receives the tubular means 7.

Referring back to the tubular member 8 which constitutes the connector 5, it is provided with a round side opening 19 for accommodating the sleeve or casing 15 of the device as depicted in FIGS. 3 and 4 and with a pair of curved wings or outwardly extending portions 20 disposed generally opposite or across from the opening 19. These wings or portions 20 are formed by providing the member with an opening opposite to the opening 19 and by cutting the member 8 along parallel lines 21 transverse to the longitudinal axis of the member and by a longitudinal parting line which extends through the opening opposite the opening 19 so that the portions 20 can be bent outwardly whereby the parting line will form marginal edges 22 on the wings and the opening opposite the opening 19 will define a pair of arcuate notches 22' interrupting the edge 22. The wing portions may be considered to be resiliently flexible or yieldable in character so that they can be manually spread apart in order that the parallel side edges of the head portions 9 will be received and gripped in the notch as evidenced in FIGS. 2, 3 and 4 to hold the device in a position substantially transverse to the longitudinal axis of the connector and/or lance so that an operator standing safely at one side or offside of the stream 2 can readily manipulate the lance to cause the entrance 14 of the device to enter the stream whereby to obtain a sample thereof as distinguished from at least some other equipment in use which requires an operator to stand in what may be termed a dangerous position to obtain a sample. The lance or member 8 may be moved with respect to one another to cause an inner end of the lance to engage the sleeve 15 of the device as best shown in FIG. 4 whereby to assist in stabilizing or holding the device in relation to the member. It should be noted that the wing portions 20 are preferably spread apart sufficiently so that the sleeve 15 of the device can be inserted into the opening 19 and the head portions 9 into the notches 22' by a single thrust of the device, or if desired the wings may be opened to a lesser extent to permit entry of the sleeve into the opening 19 so that the planar faces of the head portions will engage the opposed marginal edges 22 of the wings whereupon the device may be rotated 90° to cause the wings to spread apart in order that their notches 22' will receive the edges of the head portions. It should also be noted that the device is preferably inset from the outer end of the tubular connector a sufficient distance so that any normal charring or disintegration of the outer end resulting from engagement with any molten metal will not accidently release the device. Of further significance is the fact that the wing portions also assist in holding the half sections assembled and promote safety as they also serve as shields to protect the half sections from spraying metal as well as an operator using the device.

Figure 5:
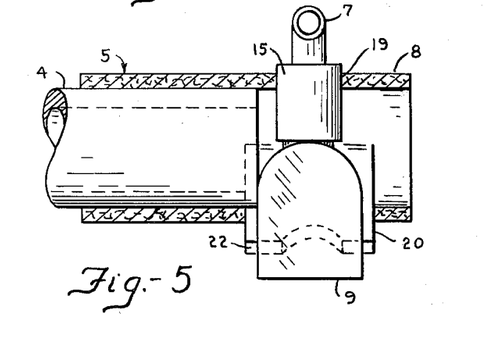
FIG. 5 is a longitudinal sectional view of a connector and a portion of a lance depicting an alternative mode of attaching the device to the connector.

If so desired, the device can be assembled with the connector as exemplified in FIG. 5, whereby the marginal end portions 22 of the wings (one shown) will engage or grip the planar side surfaces of the head portions of the sections, and an end of the lance may engage the head portions.

After a sample is obtained, the device may be readily released from the connector by merely bending back or breaking the wings and pulling the sleeve out of the opening 19 and so that the sleeve 15 and tubular means may be separated from one another including the half sections, the tubular means may be separated from a stem portion of a sample and the head portions of the sections may be released from a head portion of a sample which is joined to the stem portion.

Figures 6, 8:
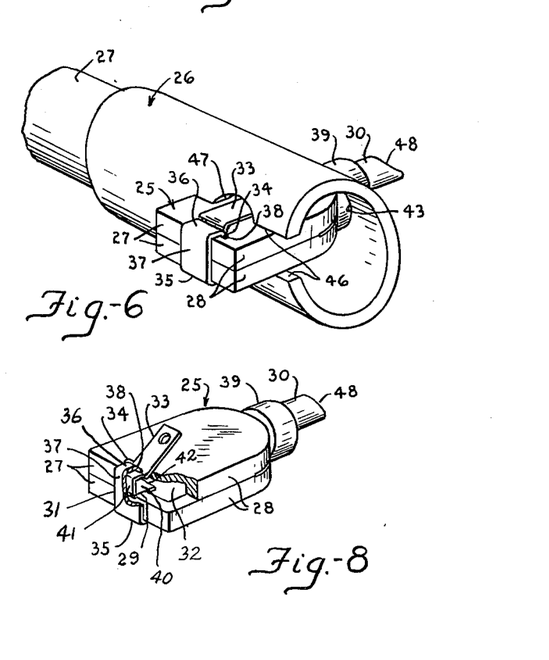
FIG. 6 is a perspective view of a modified form of connector and a sampling device which is attachable to the connector in a mode different from those shown in FIGS. 4 and 5.
FIG. 8 is a perspective view of the device shown in FIG. 6.
Figure 7:
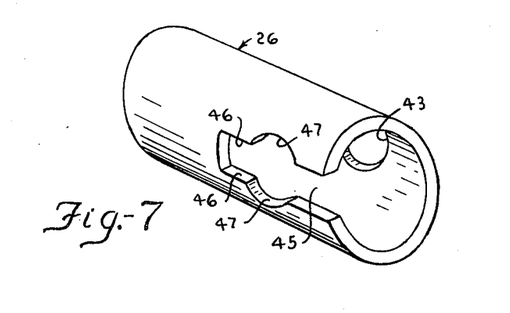
FIG. 7 is a perspective view of the connector illustrated in FIG. 6.

Referring to FIGS. 6, 7 and 8 there is disclosed a modified device generally designated 25 and a modified form of a connector generally designated 26. The connector 26 is adapted for a telescoping relatively tight fit on an end of a lance 27.

The device 25 is substantially the same as the device 6 above referred but differs therefrom in that end portions 27 of its half sections 28 are provided with notches 29 (one shown) which forms a generally rectangular opening axially aligned with the longitudinal axis of a tubular receiving means 30 and through which extends a sheet metal appendage 31, preferably rectangular in cross-section, so that an inner portion of the appendage is located in a chamber 32 formed by the head portions 28 of the sections and an outer portion 33 provided with an aperture is located exteriorly of the head portions to which a tab may be attached for identification pruposes. The notches 29 are similar to those identified as 234 in FIGS. 17 and 18. The outer planar side surfaces of the head portions 28 adjacent to the notches 29 are preferably respectively provided with transversely disposed corresponding grooves 34 (one shown) so that resiliently flexible clip means 35 having legs 36 joined by a bridge 37 embrace portions of the head portions and so that detents 38 formed on the ends of the legs may be manually located or snapped in the grooves 34. This clip means serves to hold the head portions together at one extremity of the device and a sleeve or casing 39 serves to hold the channel or extended portions at the other extremity of the device together and about the tubular means 30. The clip means also serves to cause a portion 40 of the appendage 31 to be locked in the notches 29, a portion 41 to be locked between the sections and the clip means, and an indented portion 42 of the sppendage in one of the grooves 34. This appendage and clip means are substantially the same as those shown in FIG. 15. The free outer portion 31 not only serves as a means whereby identification means may be attached thereto but is a handle which can be manually grasped or pulled by a tool whereby to release the clip means from the half sections. Obviously, the appendage per se may serve as an identification means.

The connector 26 is similar to the connector 5, described above, and is provided with a round side opening 43 which receives the sleeve 29 of the device and with an elongated notch 45 having parallel longitudinal marginal edges 46, which edges are respectively interrupted by arcuate notches 47 which define a generally round opening opposite the opening 43 whereby the head portions 28 of the device may be manually inserted into the elongated notch whereby the planar side surfaces of the head portions may be caused to engage the edges 46 to hold the device in a position substantially transverse to the longitudinal axis. The opening formed by the arcuate notches 47 obviously afford clearance to facilitate entry of the sleeve 29 through the opening 43.

The tubular means 30 is provided with a bevelled entrance 48.

Attention is directed to the fact that the plane of the bevelled entrance 48 of the device 25 is so disposed with reference to the chamber 32 formed by the head portions of the half sections that the inflow of metal or liquid into the chamber is generally more in a horizontal plane, as distinguished from a generally vertical plane when the head portions are disposed as shown in FIG. 4.

Figure 9:
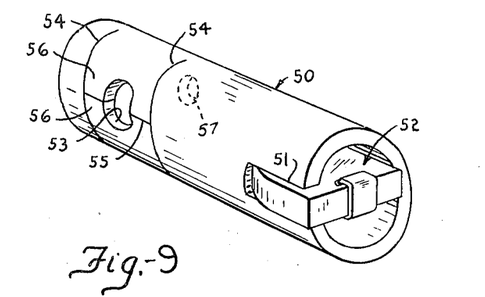
FIG. 9, depicts a perspective view of modified form of connector illustrating how the device shown in FIG. 8 can be stored therein for shipment.

A modified form of a connector generally designated 50 is depicted in FIG. 9. This connector comprises a relatively long cylindrical member having one extremity which is provided with a longitudinal slot 51 of a predetermined width and length in order to accommodate side edge portions of the head portions of half sections of a device generally designated 52, when the latter is substantially confined in the manner. This setup affords protection for the device during shipment or storage prior to use.

Figure 12:
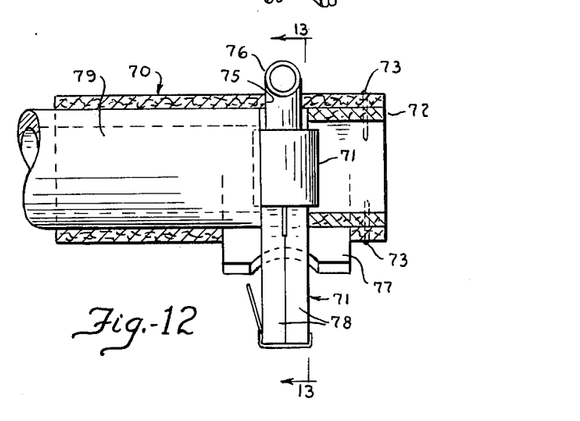
FIG. 12 is a longitudinal section of a modified form of a lance and connector and the device of FIG. 8 which is more or less jointly held against accidental displacement by the lance and connector.

The opposite extremity of the connector is provided with an opening 53 aligned with the slot 51, a pair of transverse parallel cuts or scores 54 on opposite sides of the opening and a longitudianl cut or score 55 intersecting the opening so that portions 56 of the member may be bent outwardly to provide wing portions provided with notches in a manner substantially in accord with the structure shown in FIG. 2 for accommodating the head portions of the device in either of the two positions depicted in this Figure and FIG. 5. The member is also provided with a side opening 57 opposite the opening 53 for accommodating a fore extremity of the device as shown in FIG. 12. The foregoing structure is unique in that the device is protected substantially within the confines of the connector until it is removed and installed in the connector for use. Obviously, the lance is inserted into the slotted extremity of the connector after the device is removed from its storage position and installed to its operative position.

Figure 10:
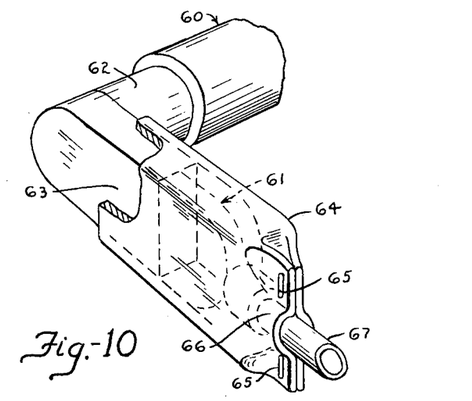
FIG. 10 is a perspective view of a modified form of a connector for a device.
Figure 11:
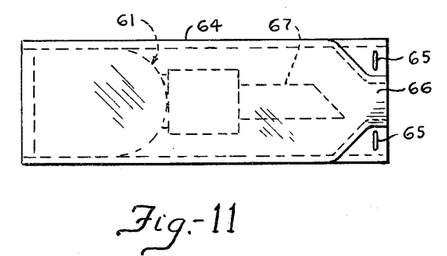
FIG. 11 is a side view of the device shown in FIG. 10.

A modified lance generally designated 60 and a modified device generally designated 61 are disclosed in FIGS. 10 and 11 of the drawing.

More particularly, FIG. 10 shows the lance provided with a generally L-shaped adapter or fitting having a cylindrical portion 62 which is telescopically tightly fitted into an end of the lance and an offset 63, generally rectangular in cross-section, for slidable reception in an open end of a generally rectangular housing 64 which contains the device and serves to protect it as described hereinafter. The opposite end of the housing is crimped, folded or formed so that portions thereof are secured together by staples 65, or equivalent means, to provide a tubular formation 66 through which a tubular means 67 of the device may be inserted for support as depicted in FIG. 10. This unique organization affords a setup whereby the device may be shifted from a dotted line inspection or storage position as in FIG. 11 or to an operative position with the tubular means 67 extended through the tubular formation 66 for use. This organization also serves to protect the device when introduced into a stream or mass of molten metal to obtain a sample and assist in preventing contamination of the sample obtained.

Figure 13:
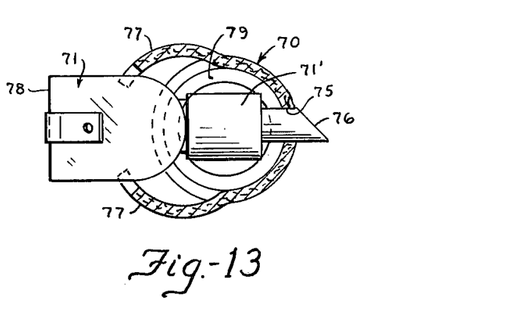
FIG. 13 is a transverse section taken substantially on line 13—13 of FIG. 12.

FIGS. 12 and 13 disclose a modified form of connector generally designated 70 for accommodating a device generally designated 71 which substantially corresponds to the device shown in FIG. 8 above referred to.

The connector 70 preferably comprises a cylindrical tubular member provided with an internal abutment means, preferably in the form of an annular ring or element 72 of pasteboard or equivalent material, which is secured in place in the member by staples 73 or equivalent means, or cement. The connector or member 70 is also provided with an opening 75 for accommodating a tubular means 76 of the device and with wings 77 opposite the opening for accommodating head portions 78 of the device. The connector is unique in that the opening 75 receives the tubular means 76 in lieu of the sleeve 71' as depicted in FIG. 3. The setup also affords a support for the tubular means in use and assists in preventing any seepage of metal or fluid into the chamber of the device between the tubular means and half sections. Another feature resides in the abutment means 72 which receives a portion of the sleeve 71' and engages one of the half sections and a portion of the sleeve is also disposed in an open end of a tubular lance 79 as depicted in FIG. 12 whereby to lock the device in a correct operative position for use. Obviously, the lance may be shifted to the position shown in FIG. 12, after the device is placed in the connector. If the abutment means is secured in position prior to entry of the device then it may become necessary to slightly cock the device so that the sleeve 71' may be correctly located in the abutment means when the wings 77 are spread apart. The device may be assembled with the connector as shown in FIGS. 12 and 13 or in a different position, such as the one shown in FIG. 5.

Figure 14:
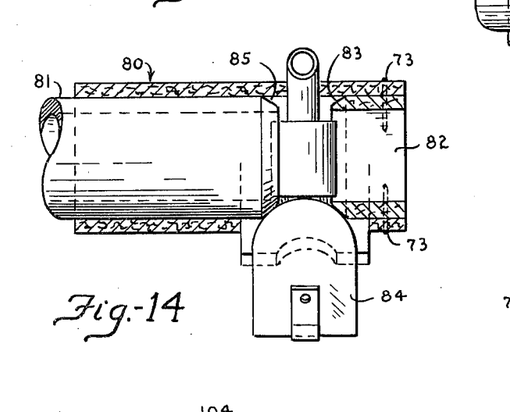
FIG. 14 is a longitudinal sectional view of a modified form of lance and connector showing another example or mode of attaching the device of FIG. 8 thereto.

FIG. 14 depicts a modified form of a connector generally designated 80 and a lance 81 which substantially respectively correspond to those shown in FIGS. 12 and 13, except that an abutment means 82 is preferably bevelled at its inner end as indicated at 83 whereby to facilitate its entry into the connector and engage curved portions of head portions of a device 84 and the inner end of the lance is preferably bevelled at 85 for also engaging the curved portions and facilitating entry of the lance into the connector, all for the purpose of holding the device in the position shown, which position is different from the one shown in FIG. 12. The lance may be shifted to the position shown to lock the device in place after the latter has been inserted into the connector.

Figure 15:
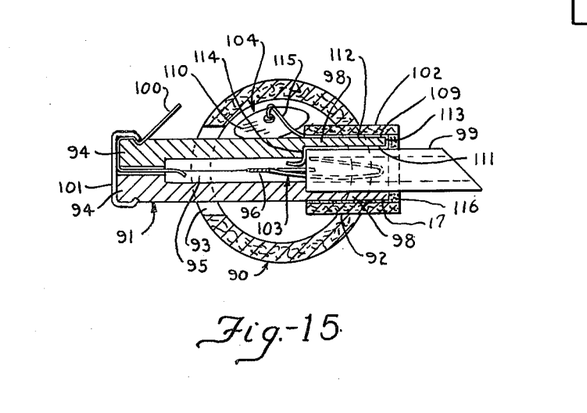
FIG. 15 is a sectional view of a connector corresponding to FIG. 7 and a modified form of device operatively connected thereto.

FIG. 15 discloses a modified form of a connector generally designated 90 and a modified device generally designated 91. The connector is provided with a pair of aligned round side openings 92 and 93 of different diameters disposed on a line transverse to the longitudinal axis of the connector.

The device 91 is quite similar to the device shown in FIG. 12, and comprises a pair of recessed half sections 94 constructed to provide a chamber 95 and side vents 96 like the vent 18 shown in FIGS. 4 and 12. These half sections also include channel portions 98 which form a tubular formation for receiving an inner extremity of a tubular means 99. The device also includes an appendage 100, clip means 101, and a sleeve 102, like those described above including a metal deoxidizing element generally designated 103 and what may be termed a trigger assembly generally designated 104.

Figure 19:
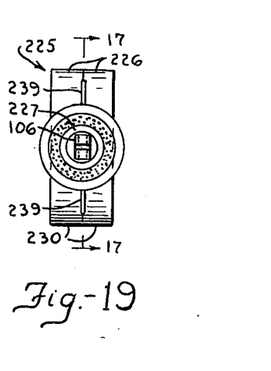
FIG. 19 is one end view of the device of FIG. 17.
Figure 20:
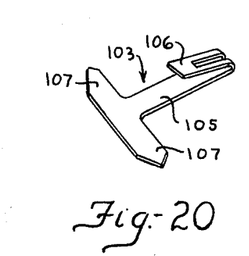
FIG. 20 is a perspective view of a deoxidizing element which may be utilized in conjunction with the device shown in FIG. 17.

The deoxidizing element 103 may be designed and constructed as desired but is preferably generally T-shaped or articulated as exemplified in FIG. 20 and includes a stem 105 having a slotted continuation 106 bent back at an acute angle over the stem and a pair of opposed portions 107 constituting the cross of the T. This element is secured in place by locating remote ends of the portions 107 in the vents and the stem 105 and its continuation 106 in the tubular means 99 so as to insure the inflow of metal will be thoroughly subjected to conditioning by the deoxidizing means both in the tubular means and chamber. The continuation 106 due to its slotted character serves to expedite melting thereof and conditioning of the metal. The free ends of the portions 107 of the element are preferably bevelled or pointed to some extent as shown in FIGS. 17 and 20 for disposition in side openings or vents 96 formed by the notches in the head portions so that some metal may flow outwardly through the vents to provide laterally extending arcuate portions 108 of a sample as depicted in FIG. 22, which will be described subsequently with respect to the device exemplified in FIGS. 17, 18 and 19.

The trigger assembly generally designated 104 is unique and preferably includes a generally U-shaped metal member 109 and a disc-like handle 110. The member has a leg 111 located between one of the portions 98 of the head sections and the tubular means 99 and a leg portion 112 between the portion 98 and the sleeve 102, a bridge portion 113 engaging an end of the portion 98, an offset inner end portion 114 extending into the chamber 95 and an outeroffset end 115 to which is connected the handle 110 or a tag. This trigger assembly affords a setup whereby after a sample has been obtained, the handle or tag can be pulled in the appropriate direction or directions whereby to assist in separating the sleeve 102 from the half sections and tubular means. It should be noted that means, such as cement or a washer 116 of pasteboard is preferably secured in the outer end of the sleeve and about the tubular means to provide a seal therebetween. It should also be noted that the side opening 92 above referred to, has a diameter to facilitate entry of the sleeve 102 of the device and that the opening 93 is larger than the opening 92 and accomodates the head or larger extremity of the device. It should be further noted that the device may be rotated about its axis relative to the connector to any position desired by an operator to facilitate entry of the tubular means into the molten metal. The tubular means 99 may be secured in place in the tubular formation formed by the channel portions 98 by the cement or as alluded to above.

Figure 17:
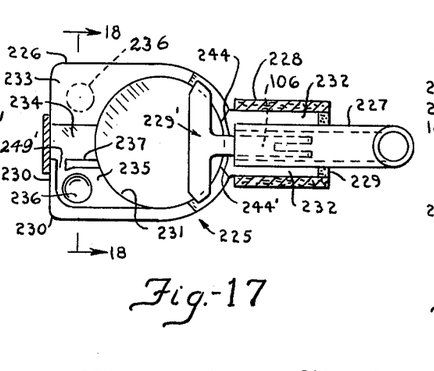
FIG. 17 is a longitudinal section taken substantially on line 17—17 of FIG. 19 of a modified device.
Figures 17A, 18:
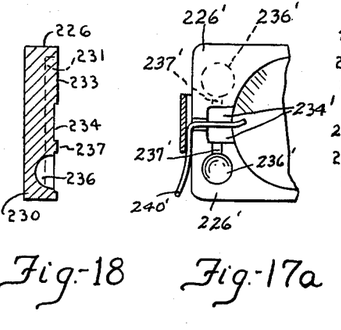
FIG. 17A is a partial inside view of a pair of half sections for use in a modified device.
FIG. 18 is a transverse section taken substantially on line 18—18 of FIG. 17.
Figure 22:
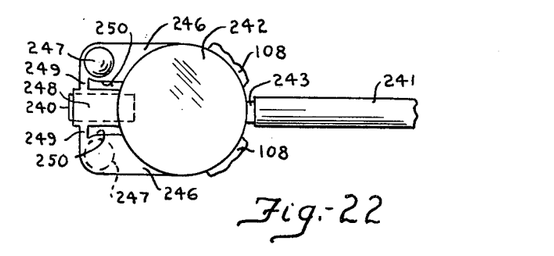
FIG. 22 is a top view of sample of molten metal obtained by using the device shown in FIG. 17.
Figure 23:
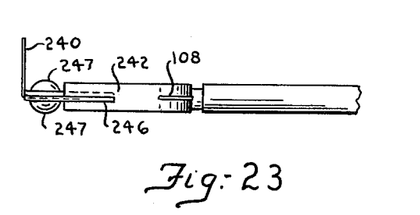
FIG. 23 is a side view of the sample shown in FIG. 22.
Figure 24:
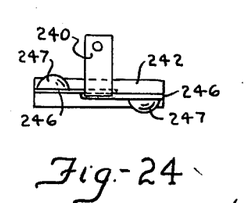
FIG. 24 is one end view of the sample depicted in FIGS. 22 and 23.
Figure 25:
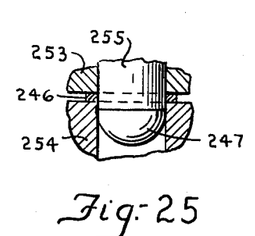
FIG. 25 is a partial sectional view showing structure and method whereby one of more portions of the sample shown in FIG. 22 may be severed therefrom.

FIGS. 17, 18 and 19 disclose a modified device generally designated 225 whereby a sample or portions may be obtained as shown in FIGS. 22, 23 and 24 and one or more portions thereof may be removed as depicted in FIG. 25. The device 225 is substantially the same as the device 90 except that it includes half sections generally designated 226 which embody different and unique structural advantages. The device does include a tubular means 227, sleeve 228, washer or cement 229 and the deoxidizing element 229' like 103.

As to the half sections 226, each comprises a generally rectangular head portion 230 provided with a round recess 231, channel portions 232 (one shown) and a solid outer end portion 233 provided with an axially extending rectangular slot 234, a relatively shallow recess 235 which is provided with a substantially semi-spherical secondary chamber or pocket 236, a longitudinally extending rib 237 constituting a side wall of the slot 234. When the sections are correctly assembled, the recesses 231 define: a primary chamber for receiving molten metal from the tubular means 227, the side notches, openings or vents 239 for the portions of the deoxidizing element 229', the axial slots 234 an opening which receives a portion of an appendage 240, as shown in FIG. 22, the shallow recesses 235 on the opposite sides of the longitudinal axis of the device respectively provide relatively broad passages through which metal may flow into the opening formed by the axial notches 234. Otherwise expressed, metal may flow from the primary chamber into the secondary chambers 236 and vents 239 so that when the metal solidifies a sample or portions will be obtained as shown in FIGS. 22, 23 and 24. An appendage 240, like the appendage 31, is preferably disposed in the axial opening for imbedment in metal and clip means is also employed for detachably holding head portions of the sections together. The size of the secondary chambers 236 are preferably predetermined so that, for example, portions obtained will each weigh one gram. However, it is to be understood that these secondary chambers may be in different sizes and shapes.

More particularly, the sample or portions illustrated in FIGS. 22, 23 and 24 include a cylindrical stem portion 241 formed in the tubular means 227, a round head portion 242 of substantially uniform thickness which may correspond to the cross-dimension of the stem portion and an intermediate restricted portion 243 formed in a passage 244 of the sections. The material defining the passage constitutes an abutment 244'. Attached to the head 242 are circumferentially spaced relatively thin outwardly extending radial portions 108 formed in the side openings or vents 239, a pair of parallel relatively thin portions 246 of uniform thickness which are located on opposite sides of and in parallel relation to the longitudinal axis of the stem. The portions 246 are formed in the receses 235 and extend in a direction opposite to that of the stem and the outer extremity of each of the portions 246 includes hemispherical portions 247 formed in the secondary chambers 236, each of which is intended to weigh, for example, one gram. It will be noted an axially extending portion 248 is formed in the opening formed by the slots 234 and that the portion 248 is joined to the outer extremities of the parallel portions 249 formed in passages 249'. It should also be noted that the head portion, parallel portions, axial portion and transverse portions define openings 250.

Figure 21:
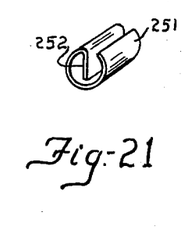
FIG. 21 is a perspective view of a modified form of a deoxidizing element which may be utilized in a mode different from that of the element shown in FIG. 20.

If found desirable, a deoxidizing element 251, as illustrated in FIG. 21, may be utilized in lieu of the element 103; for disposition in the tubular means 227. The element 251 is preferably resiliently flexible and in the form of a strip of aluminum which is rolled generally into a generally cylindrical shape and is provided with an internal portion 252. The outside diameter of the element is preferably slightly larger than the inside diameter of the tubular means 227 so the element when manually inserted into the tubular means will be automatically held in position. The element 251 is preferably adapted for disposition in the tubular means 227 and against the abutments 244' in lieu of utilizing the element 103.

FIG. 25 depicts a setup whereby a die comprising apertured members 253 and 254 may be used to obtain the sample portions 247. More specifically, in this respect the sample shown in FIG. 22 is so located that one of the portions 247 is received in an aperture of the lower die member and so that a portion 246 is clamped between the members to permit a punch 255 to sever the portion 247 from portion 246 for analysis. Obviously, any of the other portions such as 241, 242, 243 of the sample may be utilized for analysis.

Figure 22A:
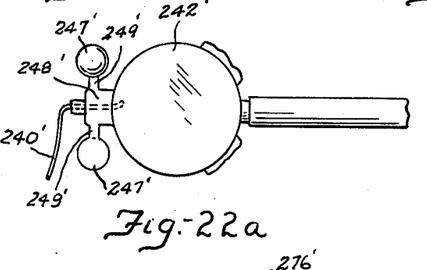
FIG. 22A is a sample obtained by utilizing the half sections depicted in FIG. 17A.

FIG. 17A illustrates a partial view of portions of a pair of half sections 226' similar to the half sections in FIG. 17 which are respectively provided with round recesses for forming a primary chamber for receiving molten metal so that a head portion 242' of a sample also having a stem is obtained as depicted in FIG. 22A. The half sections are also provided with end notches 234' which define a pocket for forming a portion 248' of the sample and with adjacent notches which define an axial opening through which a length of wire 240' extends. This wire also extends into the chamber and is preferably held in place by a clip means as clearly shown. This wire is held to the sample when the latter is formed as shown in FIG. 22A. The outer end of the wire may be provided with a tag for identifying the sample.

The half sections are further provided with semi-spherical recesses 236' which respectively provide sample portions 247' as shown in FIG. 22A. These recessed constitute secondary chambers and the molten metal flows thereto through transverse passages 237' which communicatively connect the pocket formed by the notches 234' with the secondary chambers to obtain the sample portions 247', just referred to, which are joined to the portion 248' by connecting portions 249' formed in the transverse passages 237'. Obviously, the sample portions 247' may be severed from the head portion in any manner desired, such as by the method shown in FIG. 25, as described above. The portions 247' are preferably of a size to weigh substantially one (1) gram each to facilitate analysis thereof.

Figure 26:
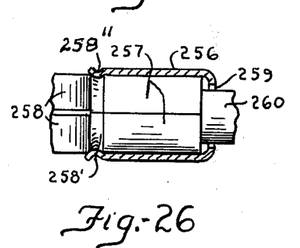
FIG. 26 is a view, partially in section of a modified way of securing half sections of a modified device together.

FIG. 26 shows a tubular casing or fastener whereby extended portions 257 of half sections 258 may be secured together in a mode different from the sleeves such as 15 and 39 above referred to. The extended portions are preferably provided with matching grooves 258' and the sleeve or fastener is preferably in the form of a metal ferrule comprising a cylindrical portion surrounding the portions 257 and an end wall provided with an opening 259 through which a tubular means 260 extends. An inner portion of the sleeve is preferably deformed into the grooves 258 as shown at 258' for locking the sections together.

Figure 27:
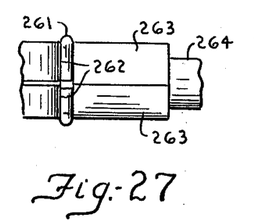
FIG. 27 is a partial view showing a different mode of securing the half sections of FIG. 26 together.

FIG. 27 is a view similar to FIG. 26 showing a different form of a fastener 261 comprising a split round flexible ring which is adapted to be manually flexed into mating grooves 262 provided in extended portions 263 of a pair of half sections for securing the sections together about a tubular means 264.

Figure 28:
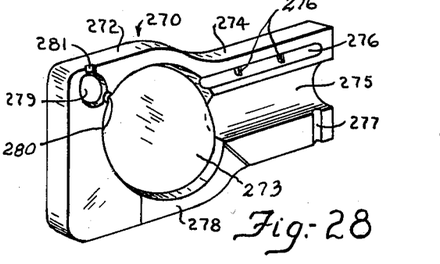
FIG. 28 is a perspective view of one of a pair of half sections of a modified device.
Figure 33:
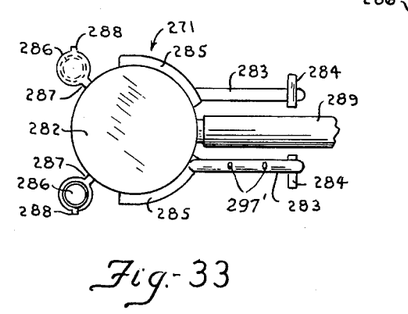
FIG. 33 is a face view of a sample obtained by using the device shown in FIG. 28.
Figure 34:
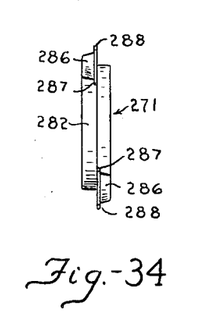
FIG. 34 is an end view of the sample shown in FIG. 33.
Figure 35:
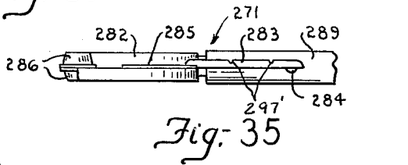
FIG. 35 is a side view of the sample shown in FIG. 33.

FIG. 28 is a perspective view of a modified form generally designated 270 of one of a pair of half sections which in combination with a tubular means, and a sleeve corresponding to those shown in FIG. 17, serve to obtain a sample generally designated 271 as exemplified in FIGS. 33, 34 and 35.

More particularly, each of the half sections 270 preferably comprises a head portion 272 provided with a large round recess 273 and a channel or extended portions 274 provided with a longitudinally extending semi-cylindrical center groove 275. The cross-dimension of the extended portion is preferably such that one side is provided with a longitudinally extending groove 276 disposed on one side of the center groove and the other side of an extended portion is provided with a transverse groove 277. The longitudinal grooves are preferably divided into three equal areas by a pair of projections or markers 276' for a purpose which will be described subsequently. The outer end of the groove 276 is closed and its inner end communicates with the recess 273. The head portion 272 of each section is also provided with a side notch 278 and with a relatively small recess 279 communicating with the round recess through a groove 180, and with the atmosphere through a groove 281.

When the sections and other components are correctly assembled to provide a device for receiving molten metal, the round recesses 273 will defined a primary chamber for forming a sample having a head 282, the longitudinal grooves 276 will form a: pair of longitudinal parallel portions 283, the tranverse grooves 277 sample portions 284 joined to portions 283, the side notches 278 a pair of lateral arcuate portions 285 joined to the head portion 282 and portions 283, the small recesses 279 truncated solid portions 286, the grooves 280 and 281 the portions 287 and 288, and a tubular means will form a stem portion 289 which is straddled by the parallel portions 283.

Attention is directed to the fact that the portions 283, 284, 287 and 288 are substantially semi-circular in cross-section and this is due to the fact that each of the grooves in each half section forming such portions cooperate with a planar portion of the other half section. For example, the longitudinal groove 276 of half section 270 is covered by an abutting planar portion of an extended portion like 274 of a mating half section (not shown). Attention is also directed to the fact that except for the center groove 275 and round recesses 273 of the sections, all of the other grooves and smaller recesses define what may be termed a plurality of secondary chambers or cavities which receive molten metal for analysis in addition to the head and stem portion of the sample. The samll truncated sample portions 286 obtained preferably have a weight of substantially one gram when severed from the head portion for analysis. It should be noted that the portions 286 are joined to the head portion by the portions 287 which are relatively thin whereby to facilitate severance of the portions and the portions 283 can also be readily severed from the head portion since they too are joined to the head by the portions 285 which relatively thin in cross-section.

Attention is also directed to the important fact that the projections or markers 276', above referred to, serve to selectively divide and measure each of the longitudinal grooves 276 into three equal areas or zones as evidenced by the resulting notches or marking 297' of the samples shown in FIGS. 33, 35, 36 and 38. Each of the sample portions 297 thereby comprise three portions which may be readily separated at the notches to obtain for example, three separate samples, each weighing one (1) gram for analysis.

Figure 29:
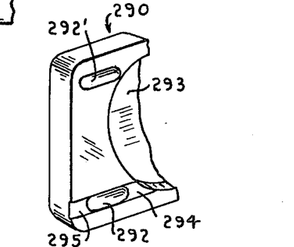
FIG. 29 is a partial perspective view of one of a pair of half sections of a modified device.
Figures 36, 37, 38, 39A, 40, 40A, 41, 42, 43:
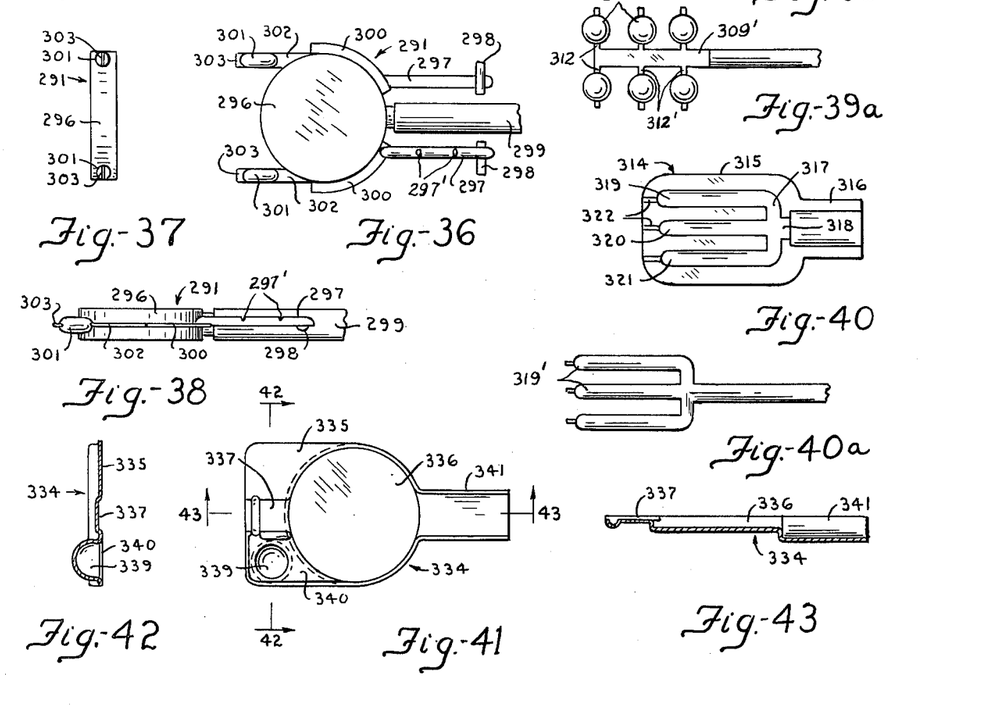
FIG. 36 is a face view of sample obtained by using the device shown in FIG. 28.
FIG. 37 is an end view of the sample shown in FIG. 36.
FIG. 38 is a side view of the sample shown in FIG. 36.
FIG. 39A is a sample obtained by utilizing a pair of half sections of the shape shown in FIG. 39.
FIG. 40 is an inside view of one of a pair of half sections of a modified device.
FIG. 40A is a sample obtained by using a pair of half sections of the character shown in FIG. 40.
FIG. 41 is an inside view of one of a pair of half sections of a modified device.
FIG. 42 is a transverse section taken substantially on line 42—42 of FIG. 41.
FIG. 43 is a longitudinal section taken substantially on line 43—43 of FIG. 41.

FIG. 29 illustrates a partial view of a modified form generally designated 290 constituting one of a pair of half sections, which pair when assembled with other components to constitute a complete sampling device, may be utilized to obtain a sample generally designated 291, as depicted in FIGS. 36, 37 and 38. More particularly each of the sections 290 is designed and constructed substantially the same as the sections 270 except for the fact that each head portion is provided with a longitudinal recess 292 and a longitudinal recess 292' which communicates with a large primary recess 293 through a groove 294 and is vented through a groove 295. The large recesses 293 define a primary chamber for obtaining a head portion 296 of the sample 291 and longitudinal grooves (not shown) will form parallel portions 297 and transverse grooves (not shown) will form transverse portions 298, and a tubular means (not shown) will form a stem portion 299. Side recesses (not shown) are provided in the head portions of of the sections to form arcuate lateral portions 300 which are joined to the portions 297. The mating grooves 292 and 292' will form relatively short solid cylindrical portions 301 which are joined to the head by fins 302 to facilitate severance of the portions 301 from the head for analysis. The portions 301 preferably have a weight of substantially one gram. The sample portions 297, 298 and 301 are obviously formed in what may be termed secondary chambers or cavities which are communicatively connected with the primary chamber and the latter to a tubular means. The grooves 295 serve as vents and form portions 303 and these portions including the portions 302 serve to facilitate severance of the portions 301 in a die structure more or less in accord with FIG. 25. What has been stated in the preceding paragraph relative to the projections 276' and notches 297' also apply to the structure and samples obtained with respect to FIGS. 29 and 36.

Figure 39:
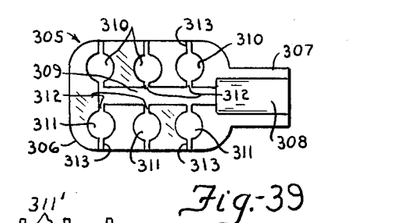
FIG. 39 is an inside view of one of a pair of half sections of a modified device.

FIG. 39 depicts an inner side view of a modified form generally designated 305 of one of a pair of half sections. Each section includes a head portion 306 and an extended portion 307 having a groove 308 therein. Each head is provided with an axially extending center groove 309, a row of three separate cavities 310 on one side of the center groove and a row or bank of three corresponding cavities 311 disposed on the other side of the center groove and in parallel relation with respect thereto. The cavities are communicatively connected with the center groove 309 by slots 312 and to the atmosphere through slots 313.

When the sections are correctly assembled with other components to complete a device the grooves 308 define a tubular formation for receiving a tubular means through which the molten metal flows to the cavities. The center grooves 309 define a center or primary chamber and the cavities 310 and 311 define secondary chambers for receiving molten metal from the center chamber and the passages 313 form vents to facilitate entry of the molten metal into the center and secondary chambers. The center grooves and cavities are preferably semi-circular in cross-section but if so desired, one of the sections may be provided with a planar inner face side for covering the grooves and cavities in the other section, in which event, the sample portions formed by the center groove and those formed in the cavities will be semi-circular in cross-section in lieu of being circular in cross-section. This organization affords a setup whereby multiportions of samples of corresponding predetermined sizes or weights may be readily obtained for analysis.

More specifically, FIGS. 39A shows a sample obtained by using a pair of assembled half sections 305. The center groove or grooves 309 for a sample portion 309' joined to a stem and portions 311' are formed in the cavities 310 and 311 and are joined to the center sample portion 309' by connecting portions 312' formed in the slots 312. Obviously, the portions 312' may serve to facilitate severance of the portions 311' for analysis.

In FIG. 40 there is disclosed a modified form of a half section generally designated 314 consistituting one of a pair of substantially corresponding half sections which form components of a complete device. Each of the sections 314 include a head 315 and an extended channel portion 316. The head of each section is preferably provided with a transverse groove 317 connected to the channel portion through a notch 318 and with three substantially corresponding longitudinal grooves 319, 320 and 321 disposed in parallel relation and having inner ends communicating with the groove 317, and with venting grooves 322 respectively extending from longitudinal grooves. When the sections 314 are assembled the longitudinal grooves define three longitudinally extending primary chambers which form sample portions having circular cross sections. Obviously, one of the half sections may have an inner planar face side for covering the grooves in the other section, in which event, the three longitudinal sample portions would be semi-circular in cross-section.

More particularly, FIG. 40A depicts a sample obtained by using a pair of half sections such as 314. The sample includes a stem portion formed in a tubular means and is joined to three substantially corresponding sample portions 319' which may be severed for analysis. It is to be understood that some of the portions obtained will vary in shape or cross-sectional dimensions, depending on the character of the secondary chambers.

Figure 30:
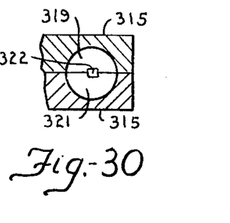
FIG. 30 is a partial sectional view of portions of a pair of assembled half sections of the shape shown in FIG. 40.
Figure 31:
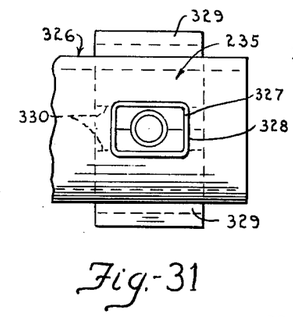
FIG. 31 is a side view of the lance, connector and a device shown in FIG. 32.
Figure 32:
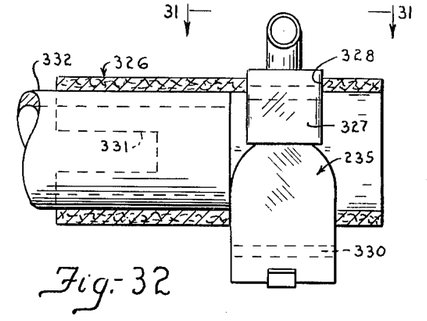
FIG. 32 is a longitudinal sectional view of a modified connector and a modified device held thereby.

FIGS. 30, 31 and 32 exemplify a modified device generally designated 325 and a connector generally designated 326, the purpose of which is to show that device may be provided with a casing 327 which is rectangular in cross-section, as distinguished from being circular; that the connector may be provided with a rectangular opening 328 for accommodating the casing; and that the connector may be also provided with flexible wing portions 329 having transverse marginal edges 330 which serve to frictionally engage opposed planar sides of head portions of the device whereby to assist in holding the latter in a substantially transverse position with respect to the longitudinal axis of the connector. One extremity of the connector is also preferably provided with a pair of opposed longitudinally extending slots 331 (one shown) whereby to facilitate entry and gripping of a lance 332 fitted therein. The inner end of the lance may be shifted to engage the device, as shown, whereby to assist in stabilizing and holding the device in place.

FIGS. 41, 42 and 43 disclose a modified structure comprising one of a pair of half sections generally designated 334. Each section is preferably in the form of a metal shell or stamping, as distinguished from the sections above described which are preferably moulded from a powdered metal. Each section includes a relatively large generally rectangular extremity 335 provided with a large circular recess 336, a semi-circular recess 339, and a relatively wide depressed portion or groove 340. The opposite extremity of each section comprises a channel portion 341 or extended portion provided with a groove. Any means suitable for the purpose may be employed to secure the extremities of the half sections together. When the sections are correctly assembled, the channel portions define a tubular formation for accommodating an inner extremity of a tubular means, and the large circular recesses 336 will define a primary chamber. The smaller recesses 339 will define a secondary chamber which receives molten metal from the primary chamber through a passage formed by the depressions 340 or grooves, and the grooves 337 will form a secondary chamber axially aligned with the tubular formation defined by the channel portions for receiving metal directly from the primary chamber. The smaller recesses 339 are so located that metal may flow into the secondary chambers formed by these recesses to form a relatively thin areas of metal surrounding the spherical sample obtained in these chambers whereby to facilitate severance or removal of the samples from the remainder for analysis.

Each of the spherical samples obtained preferably has a weight of one gram. The sections 334 may be assembled with other components, such as a tubular means and a casing in any manner desired to obtain a complete device for use. The use of sheet metal sections serves to reduce the cost of manufacturing a device as compared to those which include moulded sections of powdered metal.

It is to be understood that the half sections or receiving means can be fabricated from any material initially for the purpose, such as ceramic material, solid cast or forged metals such as copper, iron and steel, stamped from sheet metal stock. Sintered powdered metal is preferred because of certain unique characteristics it possesses. A properly designed powdered metal mold with adequate venting will form a fast chilled sample with a minimum of chemical segregation, optimum metalographic structure and precision dimensions for ease of preparation and analysis.

Elucidating further with respect to the use of the device in obtaining a sample, the sampling device is attached to the end of the lance or wand 4 so that the feed tube of the device is perpendicular to the axis of the pole. The individual taking the sample grasps the handle, faces the stream of molten metal, and holding the sample such that the feed tube of the device is near and parallel to the flow of the metal stream, twists the assembly so the open end of the feed tube is injected into the flow of the molten metal. The opening of the tube should be held at an angle to permit an unrestricted flow of the metal down the inside of the tube into the interior of the device. The open end of the tube is inserted just inside the outer surface of the stream to utilize the full volumetric capacity of the feed tube and minimize exposure of the incoming metal to the atmosphere.

As the sampling time using the invention so short, the sample size small and the mold enclosed, exposure to the atmosphere is greatly reduced, therefore reaction of the molten metal with oxygen is limited. Another important factor is the rapid transformation is accelerated by the mold design and the material employed. Rapid solidification minimizes chemical segregation and promotes a uniform structure.

It is theorized that when a molten metal sample is taken using powdered metal molds the sample is transformed quickly from the liquid to solid state by the combined action of the emissivity of the surface which allows the sintered iron mold to absorb the heat rapidly and the good conductivity of the iron allows the heat to transfer throughout the mass of the mold by conduction and convection. The good radiation characteristics of the outer surface allows for dissipation of the heat to the atmosphere. The quick chill effect of the mold design of the device coupled with its venting characteristics have permitted the design to incorporate the use of small extensions attached to the primary disc. These extensions are used primarily for the analysis of carbon and sulfur and their globular shape allows uniform cooling and solidification of the molten metal with a minimum of chemical segregation. Analysis of the elements from these samples may compare more favorably with analysis of drillings obtained from the primary disc and also with analysis obtained from product checks and possibly samples severed from glass enclosed pins which may cool differentially and have a tendency to segregate chemically.

Having thus described my invention or inventions, it is obvious that various modifications may be made in the same without departing from the spirit of the invention and, therefore, I do not wish to be understood as limiting myself to the exact forms, constructions, arrangements, and combinations of the parts herein shown and described.

I claim:

1. A device for obtaining a sample of liquid from a stream thereof, said device comprising a pair of elongated half sections, each of said sections being provided with an enlarged portion provided with a recess and a smaller channel portion, generally U-shaped clip means securing said enlarged portions together and means securing said channel portions together whereby said recesses and said channel portions respectively form a chamber and an elongated opening, and a tube having an inner extremity secured in said opening and an outer extremity provided with an entrance for a liquid for flow into said chamber via said tube.

2. The device defined in claim 1, in which said clip means has leg portions straddling said enlarged portions and said means securing said channel portions comprise a sleeve which surrounds said channel portions and assists in holding said tube in said opening.

3. The device defined in claim 1, including appendage means held between said sections by said clip means 4. A device for obtaining a sample of liquid from a supply thereof, said device comprising a pair of half sections, each of said sections having an enlarged portion provided with a recess, a notch and a small channel portion, means securing said sections together whereby said recesses, notches and channel portions respectively form a chamber, a side opening and an elongated opening, a tube having an inner extremity secured in said elongated opening and an outer extremity provided with means facilitating entry of a liquid into the tube for flow into said chamber, and generally T-shaped unitary deoxidizing means having portions respectively disposed in said chamber, said side opening and in said tube.

5. The device defined in claim 4, in which said securing means includes a sleeve surrounding said channel portions, and means is interposed between said sleeve and tube and surrounds the latter for obtaining a seal therebetween.

6. A device for obtaining a sample of liquid from a supply thereof, said device comprising wall structure forming a chamber and an elongated opening communicating with said chamber, a tube having an inner extremity disposed in relation to said opening and an outer extremity provided with an entrance for entry of a liquid into the tube for flow into said chamber, and generally T-shaped unitary deoxidizing means having articulated portions respectively disposed in said chamber and a portion in said tube.

7. The device defined in claim 6, in which said wall structure is provided with openings communicating with said chamber, and said deoxidizing means has additional portions which are respectively loosely disposed in said openings.

8. The device defined in claim 6, in which said wall structure is provided with an opening which communicates with said chamber and is located in axially spaced relation to the tube, and an appendage is held in relation to said wall structure for disposition in said opening and chamber.

9. The device defined in claim 6, in which said wall structure is provided with an opening which communicates with said chamber and is located in axially spaced relation to said tube, an appendage extends through said opening and into said chamber, clip means is secured to said wall structure and serves to lock the appendage in place, and said appendage may be utilized to assist in the release of said clip means from the wall structure.

10. A device for obtaining a sample of liquid from a supply thereof, said device including a subassembly comprising a pair of half sections, each of said sections comprising a head provided with a recess, a channel extension and resiliently flexible clip means for engaging and securing said heads whereby the recesses and extensions respectively form a chamber and an opening, and tubular means having an inner extremity secured in relation to said opening and an outer extremity provided with an entrance whereby liquid may be caused to flow through said tubular means into said chamber.

11. The device defined in claim 10, in which each of said sections is also provided with a secondary recess and a groove which respectively form secondary chambers and passages which establish communication between said first mentioned chamber and said secondary chambers.

12. The device defined in claim 10, in which the head of each section is provided with an outwardly extending groove which communicates with said chamber, including a recess forming a secondary chamber and a groove which establishes communication between said secondary chamber and said outwardly extending groove.

13. A subassembly of a device for obtaining a sample of liquid from a supply thereof, said subassembly comprising wall structure forming a head and an extension, said head being provided with a pair of parallel longitudinal passages which are enlarged intermediate their extremities to provide a pair of chambers, said extension being provided with a longitudinal opening which is communicatively connected to said chambers through said passages, and said head is also provided with a passage connected to said pair of passages for venting said chambers.

14. An elongated molten metal sample comprising a head portion, a stem portion joined to and extending from said head portion, and a portion offset from the longitudinal axis of said sample joined to said head portion at a location remote from said stem portion by a intermediate restricted portion whereby to facilitate severance of said offset portion from said head portion.

15. A molten metal sample comprising a head portion, an elongated stem portion joined to and extending from said head portion, and a pair of offset portions respectively joined to said head portion at locations remote from one aother and said stem portion by a pair of relatively thin intermediate restricted portions whereby to facilitate severance of said offset portions from said head portion.

16. A molten metal sample comprising a head portion, a stem portion joined to said head portion and extending in one direction therefrom, offset portions joined to said head portion by intermediate restricted portions extending in different directions, and an additional portion joined to said head portion and extending therefrom in an axially aligned direction away from said stem portion.

17. A subassembly for use as a component of a device for obtaining a sample of molten material by insertion into a supply thereof, said subassembly comprising wall structure forming an enlargement provided with internal surfaces forming a primary chamber and a reduced tubular formation having an entrance, and said enlargement having a outer end area provided with internal surfaces forming a secondary smaller chamber offset from said primary chamber and a passage whereby molten material entering said entrance will flow through said passage into said secondary chamber via said primary chamber for eventual solidificaton against the internal surfaces of said chambers to provide a sample having a large portion, a smaller portion, and a intermediate restricted portion joining said large and smaller portions within the confines of said enlargement and outer end area thereof.

18. A structure for use as a means of a device for obtaining a sample of molten material from a supply thereof, said structure comprising walls forming an enlargement provided with internal surfaces forming a primary chamber having an entrance, said enlargement also being provided with internal surfaces forming a secondary chamber and a passage whereby the molten material entering said entrance will flow therefrom successively into said primary chamber and into said secondary chamber via said passage for eventual solidification against the internal surfaces thereof whereby to form a sample substantiallly within the confines of said chambers which has a large portion and a smaller portion of a predetermined size which is joined to said large portion by an intermediate restricted portion, and said enlargement being provided with a tortuous passage for venting said secondary chamber.

19. A structure for use as a means of a device for obtaining a sample of molten material from a supply thereof, said structure comprising walls forming an enlargement provided with internal surfaces forming a plurality of communicatively connected chambers and an entrance communicatively connected to all chambers for receiving material for flow into said chambers and against said surfaces for solidification therein, and said enlargement having a passage which is common to said chambers for venting the latter whereby to facilitate the flow of the molten material into said chambers whereby the material when solidified will form a sample disposed substantially entirely within the confines of said chambers.

20. Deoxidizing means adapted for use in a device for obtaining a sample of molten metal, said means being generally T-shaped to include a stem, a pair of wing portions joined to and projecting laterally from one end of said stem, and said stem being provided with a continuation bent back over the stem at an angle with respect thereto.

21. A method which comprises obtaining a sample of molten metal having a head and a portion of predetermined weight joined to said head, locating the portion in die means, and punching said portion from said head through the agency of said die means.

22. A molten metal sample having a head, a stem joined to said head, an axial portion joined to said head and spaced from said stem, and a pair of portions extending laterally from said axial portion.

23. A subassembly of a device for obtaining a sample of molten metal, said subassembly comprising a pair of elongated members which when assembled form a chamber for receiving molten metal and a tubular portion through which the metal flows into the chamber, means respectively embracing portions of the extremities of said members for holding the members assembled, and one of said means being in the form of a substantially U-shaped clip.

24. A device for obtaining a sample of molten material by insertion into such material, said device comprising wall structure provided with a primary chamber and a tubular entrance through which such a material may be caused to flow into said chamber, said structure also having an end area provided with a secondary smaller chamber offset from said primary chamber, and a restricted passage through which the material may be controlled for flow into said secondary chamber whereby the material upon solidification will form a sample comprising a relatively large portion and a smaller portion joined to said large portion by an intermediate restricted portion.

25. Deoxidizing means adapted for use in a device for obtaining a sample of molten metal, said means being generally T-shaped to include a stem and a pair of lateral portions.

26. A subassembly of a device for obtaining a sample of molten material from a supply thereof, said subassembly comprising a pair of elongated complementary sections forming; a primary chamber having a entrance, a secondary chamber, a first passage disposed opposite said entrance and communicating with said primary chamber and the atmosphere, and a second passage communicatively connecting said second chamber with said first passage.

27. The subassembly defined in claim 26, including a third chamber communicatively connected to said first passage.

28. A molten metal sample comprising a head portion, a stem portion joined to and extending from said head portion, a portion joined to said head portion and extending therefrom in an axial direction away from said stem portion, and an additional portion joined to said axially extending portion by an intermediate restricted portion.

29. The sample defined in claim 28, in which said additional portion is joined to said head portion by an intermediate restricted portion.

30. The sample defined in claim 28, including means connected to said axially extending portion for identification purposes.

* * * * *